(12) United States Patent
Bor

(10) Patent No.: US 12,582,552 B2
(45) Date of Patent: Mar. 24, 2026

(54) DETERMINING RADIANT EXPOSURE AT THE RETINA DURING AN OPHTHALMIC PROCEDURE

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 645 days.

(21) Appl. No.: 17/938,877

(22) Filed: Oct. 7, 2022

(65) Prior Publication Data

US 2023/0157878 A1     May 25, 2023

Related U.S. Application Data

(60) Provisional application No. 63/281,259, filed on Nov. 19, 2021.

(51) Int. Cl.
 A61F 9/008          (2006.01)

(52) U.S. Cl.
 CPC ...... A61F 9/008 (2013.01); *A61F 2009/0087* (2013.01)

(58) Field of Classification Search
 CPC ............................................. A61F 9/008–009
 See application file for complete search history.

(56) References Cited

U.S. PATENT DOCUMENTS

| | | | |
|---|---|---|---|
| 3,780,979 A | 12/1973 | De | |
| 4,357,088 A | 11/1982 | Pomerantzeff | |
| 5,312,396 A | 5/1994 | Feld | |
| 5,909,270 A | 6/1999 | Moser | |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Adrian G.H. Podoleanu et al., Combined optical coherence tomograph and scanning laser ophthalmoscope mi nije dostupan besplatno., Electronics Letters, 34 (11), 1998.

(Continued)

*Primary Examiner* — Lynsey C Eiseman
(74) *Attorney, Agent, or Firm* — Patterson + Sheridan, LLP

(57)     ABSTRACT

In certain embodiments, an ophthalmic laser system includes a laser device, an ophthalmic microscope, a z-direction sensor, and a controller. The laser device directs a laser beam towards a target within an eye. The ophthalmic microscope receives light from a focal point within the eye to provide an image of an object at the focal point. The z-direction sensor determines the z-position corresponding to the focal point of the ophthalmic microscope. The controller determines a position $Z_0$, the z-position where the focal point of the ophthalmic microscope is at the retina of the eye; determines a position Z, the z-position where the focal point of the ophthalmic microscope is at the target within the eye; calculates a target-to-retina distance $\Delta Z$ according to a difference between the position Z and the position $Z_0$; and calculates a radiant exposure $H_e$ at the retina according to the target-to-retina distance $\Delta Z$.

11 Claims, 3 Drawing Sheets

(56)  References Cited

U.S. PATENT DOCUMENTS

| | | | |
|---|---|---|---|
| 6,142,630 | A | 11/2000 | Koester |
| 6,322,556 | B1 | 11/2001 | Gwon |
| 6,789,900 | B2 | 9/2004 | Van |
| 7,374,287 | B2 | 5/2008 | Van |
| 7,510,282 | B2 | 3/2009 | Ueno |
| 7,520,613 | B2 | 4/2009 | Saito et al. |
| 7,703,922 | B2 | 4/2010 | Van |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0103010 | A1* | 4/2013 | Grant .................. A61F 9/00825 |
| | | | 606/4 |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |
| WO | 2023089459 A1 | 5/2023 |
| WO | 2023097391 A1 | 6/2023 |

(56) References Cited

FOREIGN PATENT DOCUMENTS

OTHER PUBLICATIONS

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.

Nidek, Scanning Laser Ophthalmoscope Mirante SLO/OCT Mirante SLO, https://www.nidek-intl.com/product/ophthaloptom/diagnostic/dia_retina/mirante.htm.

Peter G. J. Barten, "Contrast Sensitivity of the Human Eye and its Effects on Image Quality," Chapter 3, pp. 27-40, Model for the spatial contrast sensitivity of the eye, (1999).

Pointer, J. S., & Hess, R. F. "The contrast sensitivity gradient across the human visual field: With emphasis on the low spatial frequency range,", R. F. Vision Research, 29(9), 1133-1151 (1989).

Sebag J et al., Vitreous and Vitreoretinal Interface, Ch. 21, 2015.

Sebag J., Vitreous and Vision Degrading Myodesopsia. Progress in Retinal and Eye Research Nov. 2020;79.

T Ivanova et al, Vitrectomy for primary symptomatic vitreous opacities: an evidence-based review, Eye (Lond) May 2016;30(5):645-55.

Teri T Kleinberg et al., Vitreous substitutes: a comprehensive review, Survey of Ophthalmology, 56 (4), 2011.

Damodaran et al., "Digital micromirror device based ophthalmoscope with concentric circle scanning", 2017, pp. 2766-2780, vol. 8, No. 5, Biomedical Optics Express.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering GMBH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, PLOS ONE.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3×3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&pr_ref_pid=4513048952866&pr_seq=uniform.

Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;amp;_sid=b50c0674f&amp;amp;_ss=r.

Wang et al., "In vivo full range complex Fourier domain optical coherence tomography", Jan. 30, 2007, 054103, vol. 90, Applied Physics Letters.

Wojtkowski et al., "Full range complex spectral optical coherence tomography technique in eye imaging", 2002, pp. 1415-1417, vol. 27, No. 16, Optics Letters.

Yasuno et al., "Simultaneous B—M—mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacitiesby Light-Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

(56) References Cited

OTHER PUBLICATIONS

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/rloater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

* cited by examiner

DETERMINING RADIANT EXPOSURE AT THE RETINA DURING AN OPHTHALMIC PROCEDURE

TECHNICAL FIELD

The present disclosure relates generally to ophthalmic systems and methods, and more particularly to ophthalmic systems and methods for determining radiant exposure at the retina during an ophthalmic procedure.

BACKGROUND

During ophthalmic laser surgery, a surgeon may direct a laser beam into the eye to treat the eye. For example, a laser beam may be directed into the vitreous to remove eye floaters. Eye floaters are clumps of collagen proteins that form in the vitreous. These clumps disturb vision with moving shadows and distortions, and sometimes they block vision. The laser beam may be used to disintegrate the floaters, thus improving vision. However, as with any ophthalmic laser surgery, care must be taken to avoid overexposing the eye to laser radiation.

BRIEF SUMMARY

In certain embodiments, an ophthalmic laser system includes a laser device, an ophthalmic microscope, a z-direction sensor, and a controller. The laser device directs a laser beam towards a target within an eye that has a retina. An axis of the eye defines a z-axis, where a z-position is a position relative to the z-axis. The ophthalmic microscope receives light from a focal point within the eye to provide an image of an object at the focal point. The z-direction sensor determines the z-position corresponding to the focal point of the ophthalmic microscope. The controller: determines a position $Z_0$, the z-position where the focal point of the ophthalmic microscope is at the retina of the eye; determines a position $Z$, the z-position where the focal point of the ophthalmic microscope is at the target within the eye; calculates a target-to-retina distance $\Delta Z$ according to a difference between the position $Z$ and the position $Z_0$; and calculates a radiant exposure $H_e$ at the retina according to the target-to-retina distance $\Delta Z$.

Embodiments may include none, one, some, or all of the following features:

The z-direction sensor determines the z-position corresponding to the focal point of the ophthalmic microscope by detecting the z-position of a base of the ophthalmic microscope.

The controller determines the position $Z_0$, the z-position where the focal point of the ophthalmic microscope is at the retina of the eye, by: autofocusing the focal point of the ophthalmic microscope at the retina of the eye; and determining, from the z-direction sensor, the z-position corresponding to the focal point.

The controller determines the position $Z_0$, the z-position where the focal point of the ophthalmic microscope is at the retina of the eye, by: receiving user input that the focal point of the ophthalmic microscope is at the retina of the eye; and determining, from the z-direction sensor, the z-position corresponding to the focal point.

The controller determines the position $Z$, the z-position where the focal point of the ophthalmic microscope is at the target within the eye, by: autofocusing the focal point of the ophthalmic microscope at the target within the eye; and determining, from the z-direction sensor, the z-position corresponding to the focal point.

The controller determines the position $Z$, the z-position where the focal point of the ophthalmic microscope is at the target within the eye, by: receiving user input that the focal point of the ophthalmic microscope is at the target within the eye; and determining, from the z-direction sensor, the z-position corresponding to the focal point.

The controller calculates the radiant exposure $H_e$ according to the target-to-retina distance $\Delta Z$ by: determining a laser spot size of the laser beam on the retina; and calculating the radiant exposure $H_e$ according to the target-to-retina distance $\Delta Z$ and the laser spot size of the laser beam.

The controller further calculates: a closest target-to-retina distance $\Delta Z$ at which the eye can be treated, given a laser pulse energy E of the laser beam; a maximum laser pulse energy E at which the eye can be treated, given the target-to-retina distance $\Delta Z$; and/or a range of laser pulse energy E values and a range of target-to-retina distance $\Delta Z$ values at which the eye can be treated.

The controller further: determines whether the radiant exposure $H_e$ exceeds a maximum radiant exposure; if the radiant exposure $H_e$ exceeds a maximum radiant exposure, prevents the laser device from directing the laser beam towards the target within the eye; and otherwise, allows the laser device to direct the laser beam towards the target within the eye.

In certain embodiments, a method directs a laser beam towards a target within an eye that has a retina. An axis of the eye defines a z-axis, where a z-position is a position relative to the z-axis. The method includes: receiving, at an ophthalmic microscope, light from a focal point within the eye to provide an image of an object at the focal point; determining, by a z-direction sensor, the z-position corresponding to the focal point of the ophthalmic microscope; determining, by a controller, a position $Z_0$, the z-position where the focal point of the ophthalmic microscope is at the retina of the eye; determining a position $Z$, the z-position where the focal point of the ophthalmic microscope is at the target within the eye; calculating a target-to-retina distance $\Delta Z$ according to a difference between the position $Z$ and the position $Z_0$; and calculating a radiant exposure $H_e$ at the retina according to the target-to-retina distance $\Delta Z$.

Embodiments may include none, one, some, or all of the following features:

The determining, by the z-direction sensor, the z-position corresponding to the focal point of the ophthalmic microscope further comprises detecting the z-position of a base of the ophthalmic microscope.

The determining, by the controller, the position $Z_0$, the z-position where the focal point of the ophthalmic microscope is at the retina of the eye, further comprises: autofocusing the focal point of the ophthalmic microscope at the retina of the eye; and determining, from the z-direction sensor, the z-position corresponding to the focal point.

The determining, by the controller, the position $Z_0$, the z-position where the focal point of the ophthalmic microscope is at the retina of the eye, further comprises: receiving user input that the focal point of the ophthalmic microscope is at the retina of the eye; and determining, from the z-direction sensor, the z-position corresponding to the focal point.

The determining the position Z, the z-position where the focal point of the ophthalmic microscope is at the target within the eye, further comprises: autofocusing the focal point of the ophthalmic microscope at the target within the eye; and determining, from the z-direction sensor, the z-position corresponding to the focal point.

The determining the position Z, the z-position where the focal point of the ophthalmic microscope is at the target within the eye, further comprises: receiving user input that the focal point of the ophthalmic microscope is at the target within the eye; and determining, from the z-direction sensor, the z-position corresponding to the focal point.

The calculating the radiant exposure $H_e$ according to the target-to-retina distance $\Delta Z$ further comprises: determining a laser spot size of the laser beam on the retina; and calculating the radiant exposure $H_e$ according to the target-to-retina distance $\Delta Z$ and the laser spot size of the laser beam.

The method further comprises: calculating a closest target-to-retina distance $\Delta Z$ at which the eye can be treated, given a laser pulse energy E of the laser beam; a maximum laser pulse energy E at which the eye can be treated, given the target-to-retina distance $\Delta Z$; and/or a range of laser pulse energy E values and a range of target-to-retina distance $\Delta Z$ values at which the eye can be treated.

The method further comprises: determining whether the radiant exposure $H_e$ exceeds a maximum radiant exposure; if the radiant exposure $H_e$ exceeds a maximum radiant exposure, preventing the laser device from directing the laser beam towards the target within the eye; and otherwise, allowing the laser device to direct the laser beam towards the target within the eye.

In certain embodiments, an ophthalmic laser system includes a laser device, an ophthalmic microscope, a z-direction sensor, and a controller. The laser device directs a laser beam towards a target within an eye that has a retina. An axis of the eye defines a z-axis, where a z-position is a position relative to the z-axis. The ophthalmic microscope receives light from a focal point within the eye to provide an image of an object at the focal point. The z-direction sensor determines the z-position corresponding to the focal point of the ophthalmic microscope by detecting the z-position of a base of the ophthalmic microscope. The controller determines a position $Z_0$, the z-position where the focal point of the ophthalmic microscope is at the retina of the eye by: autofocusing the focal point of the ophthalmic microscope at the retina of the eye or receiving user input that the focal point of the ophthalmic microscope is at the retina of the eye; and determining, from the z-direction sensor, the z-position corresponding to the focal point. The controller determines a position Z, the z-position where the focal point of the ophthalmic microscope is at the target within the eye, by: autofocusing the focal point of the ophthalmic microscope at the target within the eye or receiving user input that the focal point of the ophthalmic microscope is at the target within the eye; and determining, from the z-direction sensor, the z-position corresponding to the focal point. The controller calculates a target-to-retina distance $\Delta Z$ according to a difference between the position Z and the position $Z_0$. The controller calculates a radiant exposure $H_e$ at the retina according to the target-to-retina distance $\Delta Z$ by: determining a laser spot size of the laser beam on the retina; and calculating the radiant exposure $H_e$ according to the target-to-retina distance $\Delta Z$ and the laser spot size of the laser beam. The controller also calculates: a closest target-to-

4 retina distance $\Delta Z$ at which the eye can be treated, given a laser pulse energy E of the laser beam; a maximum laser pulse energy E at which the eye can be treated, given the target-to-retina distance $\Delta Z$; and a range of laser pulse energy E values and a range of target-to-retina distance $\Delta Z$ values at which the eye can be treated. The controller also: determines whether the radiant exposure $H_e$ exceeds a maximum radiant exposure; if the radiant exposure $H_e$ exceeds a maximum radiant exposure, prevents the laser device from directing the laser beam towards the target within the eye; and otherwise, allows the laser device to direct the laser beam towards the target within the eye.

DESCRIPTION OF EXAMPLE EMBODIMENTS

Figure 1:
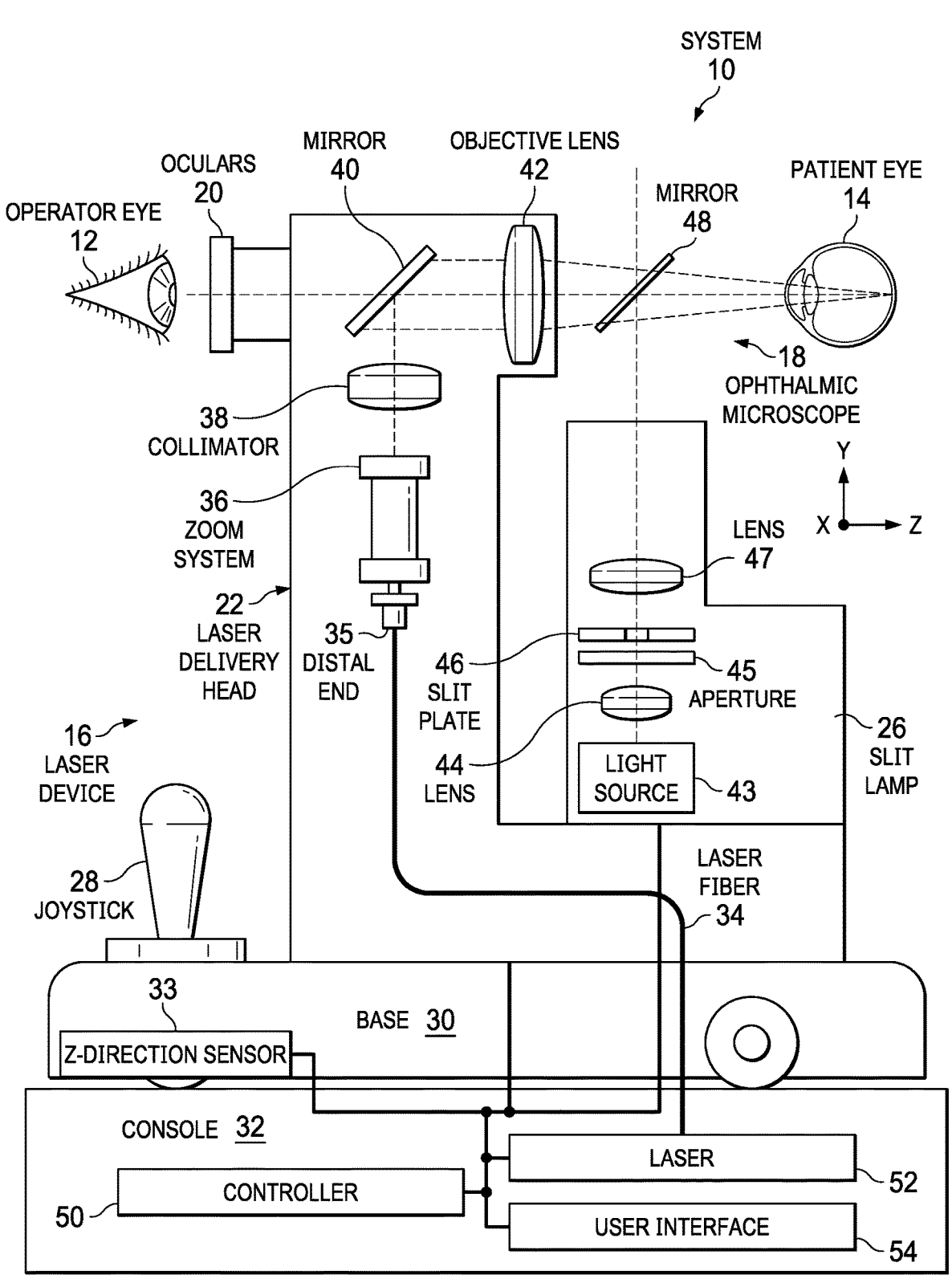
FIG. 1 illustrates an example of an ophthalmic laser system, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, an ophthalmic laser system avoids overexposing the retina to laser radiation during an ophthalmic procedure. The laser system has a laser device, an ophthalmic microscope, and a z-direction sensor. The z-direction sensor measures the z-position of a base plate of the system. The z-position of the base plate indicates the z-position of the focal point of the microscope and thus the z-position of an object (e.g., a floater or the retina) on which the microscope is focused. In the embodiments, the z-direction sensor is used to determine the distance between a target (such as a floater) and the retina. The laser system calculates radiant exposure at the retina from the distance to the retina, and uses the calculated radiant exposure to take steps to avoid overexposing the retina to radiation that exceeds a maximum radiant exposure.

FIG. 1 illustrates an example of an ophthalmic laser system 10, according to certain embodiments. Ophthalmic laser system 10 allows an operator (with an operator eye 12) to perform an ophthalmic laser procedure on a patient eye 14 of a patient. In certain situations, ophthalmic laser system 10 is used to perform laser vitreolysis to direct a laser beam to targets in the vitreous, such as vitreous floaters. Ophthalmic laser system 10 allows the operator to see floaters within the eye, and then direct a laser beam to fragment the floaters.

In the illustrated example, ophthalmic laser system 10 comprises oculars 20, a laser delivery head 22, an illuminator (such as a slit lamp 26), a positioning device (such as a joystick 28), a base 30, a z-direction sensor 33, and a console 32, coupled as shown. Laser delivery head 22 includes a laser fiber 34 (with a distal end 35), a zoom system 36, a collimator 38, a mirror 40, and an objective lens 42, coupled as shown. Slit lamp 26 includes a light source 43, condenser lens 44, a variable aperture 45, a variable slit plate 46, a projection lens 47, and a mirror 48. Console 32 includes a computer (such as a controller 50), a laser 52, and a user interface 54, coupled as shown.

As an overview, ophthalmic laser system 10 includes a laser device 16 (e.g., laser 52, laser fiber 34, and laser delivery head 22) and an ophthalmic microscope 18 (e.g., oculars 20, objective lens 42, mirror 48, and slit lamp 26). Operator eye 12 utilizes the optical path from oculars 20 through mirror 40, objective lens 42, and mirror 48 to view patient eye 14. A laser beam follows the laser path from laser 52 through laser delivery head 22 and mirror 48 to treat patient eye 14.

According to the overview, the laser device directs a laser beam towards a target within patient eye 14. An axis of eye 14 (e.g., visual or optical) defines a z-axis. A z-position of an object is the position of the object relative to the z-axis. Ophthalmic microscope 18 receives light reflected from a focal point within eye 14 to provide an image of an object at the focal point. Z-direction sensor 33 determines the z-position corresponding to the focal point of the ophthalmic microscope. Controller 50 determines z-position $Z_0$, where the focal point of the ophthalmic microscope is at the retina of eye 14, and z-position Z, where the focal point of the ophthalmic microscope is at the target within eye 14. Controller 50 calculates a target-to-retina distance ΔZ by calculating a difference between z-position Z and z-position $Z_0$, and calculates the radiant exposure $H_e$ at the retina according to the target-to-retina distance ΔZ.

In more detail, in certain embodiments, oculars 20 allow operator eye 12 to view patient eye 14. Laser delivery head 22 delivers a laser beam from laser 52 of console 32 to patient eye 14. Laser fiber 34 of delivery head 22 transports the laser beam from laser 52 to the distal end 35 of fiber 34. Zoom system 36 includes optical elements that change the spot size of the laser beam that exits distal end 35 of fiber 34. An optical element can act on (e.g., transmit, reflect, refract, diffract, collimate, condition, shape, focus, modulate, and/or otherwise act on) light. Collimator 38 collimates the laser beam, and mirror 40 directs the beam through objective lens 4, which focuses the beam.

The illuminator of laser system 10 provides light that illuminates the surgical site of patient eye 14. In certain embodiments, the illuminator comprises a slit lamp. Slit lamp 26 includes light source 43, which emits light such as a high-intensity illumination light. Condenser lens 44 directs the light towards variable aperture 45 and variable slit plate 46. Variable aperture 45 defines the height of the light in the y-direction, and variable slit plate 43 defines the width of the light in the x-direction to form the light into a slit shape. Projection lens 47 directs the light towards prism mirror, which directs the slit of light into patient eye 14.

Base 30 supports laser delivery head 22 and slit lamp 24. Joystick 28 moves base 30 in the x- and z-directions. Console 32 includes components that support the operation of system 10. Controller 50 of console 32 is a computer that controls of the operation of components of system 10, e.g., joystick 28, base 30, laser delivery head 22, slit lamp 26, laser 52, and/or user interface 54. For example, in response to instructions from joystick 28, controller 50 moves the laser delivery head 22, according to the instructions. Laser 52 supplies the laser beam that has a cone-shaped energy profile that focuses energy onto a point. Any suitable laser 30 may be used, e.g., a femtosecond or nanosecond laser with any suitable crystal (e.g., Nd:YAG, Erbium:YAG, Ti:Sapphire, or ruby). The laser beam may have any suitable wavelength, e.g., in a range from 500 nm to 1200 nm. User interface 54 communicates information between the operator and system 10.

Z-direction sensor 33 determines the z-position corresponding to the focal point of ophthalmic microscope 18 by detecting movement of base 30. Z-direction sensor 33 may be any suitable sensor that can detect movement of base 30. Examples of such sensors include linear, capacitive, inductive, Hall-effect based, magnetic, magneto-resistive, optical, ultrasound, interferometric, grating based, and/or image-based sensors. In some examples, the sensor may be a rotary sensor that detects movement of the rack and pinion of slit lamp 26.

Figure 2:
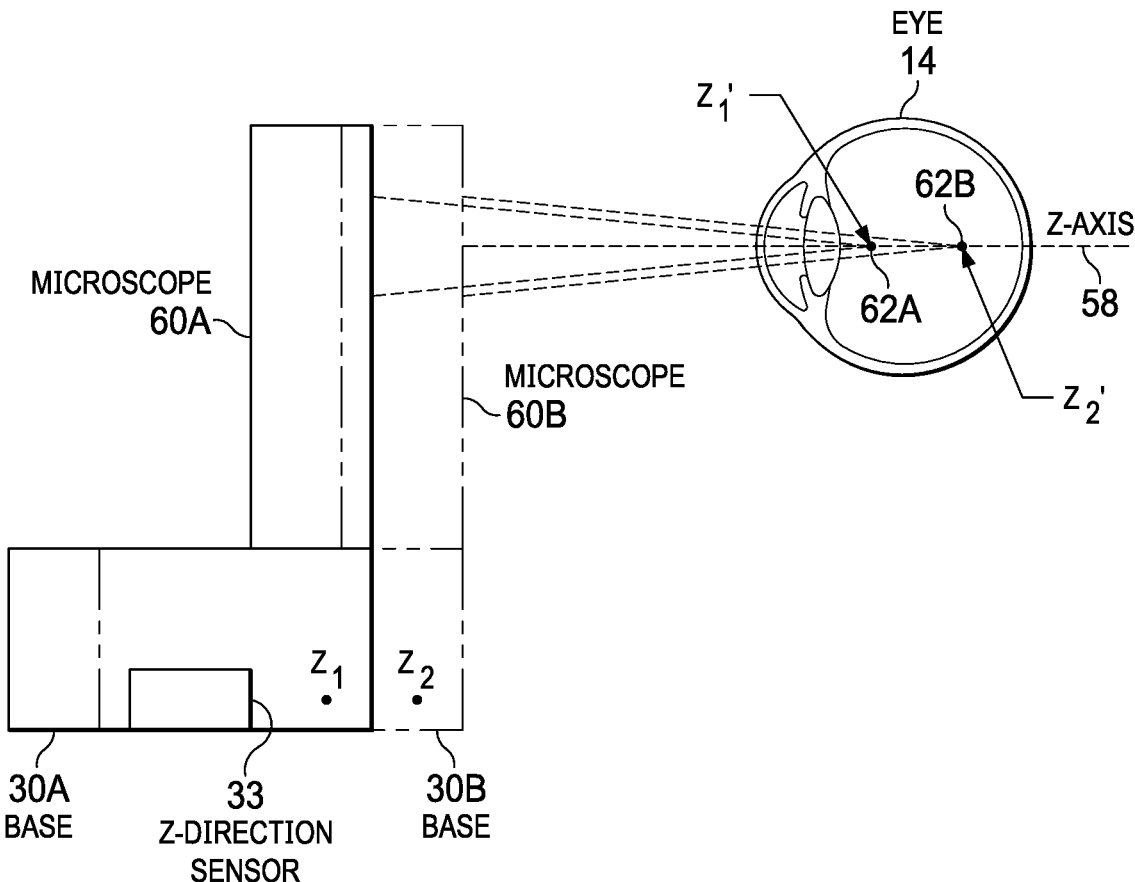
FIG. 2 illustrates an example of z-direction sensor that determines the z-position corresponding to the focal point focal point of the ophthalmic microscope of the ophthalmic laser system of FIG. 1, according to certain embodiments.

FIG. 2 illustrates an example of z-direction sensor 33 that determines the z-position corresponding to the focal point focal point 62 (62a, 62b) of the ophthalmic microscope 60 (60a, 60b) of ophthalmic laser system 10 of FIG. 1, according to certain embodiments. In certain embodiments, z-direction sensor 33 determines the z-position corresponding to the focal point within eye 14 by detecting the z-position of a base 30 (30a, 30b) of the ophthalmic microscope. Base 30 moves one or more components (e.g., the objective lens 42) of ophthalmic microscope 16 that determine the focal point of microscope 16, such that the movement of base 30 indicates movement of the focal point of microscope 16.

In the illustrated example, eye 14 has an axis (e.g., visual or optical) that defines a z-axis 58. In the example, base 30 is at a particular z-position when a specific point of base 30 is at the z-position. For example, base 30a is at z-position $z_1$ because a point of base 30 is at z-position $z_1$, and base 30b is at z-position $z_2$ because that point of base 30 is at z-position $z_2$. Z-direction sensor 33 records the z-position of base 30.

The z-position of base 30 indicates the z-position of the focal point 62 of the ophthalmic microscope 60. For example, base 30a at z-position $z_1$ indicates that focal point 62a is at z-position $z'_1$, and base 30b at z-position $z_2$ indicates that focal point 62b is at z-position $z'_2$. Accordingly, the z-position z of base 30 also indicates the z-position z' of an object on which microscope 60 is focused. An object may be a feature of the eye (e.g., the retina) or a target (e.g., a floater) within the eye. Moreover, the difference between the z-positions z1-z2 of base 30 may be at least proportional to or equivalent to the difference between the z-positions z'1-z'2 of focal points 62 or objects on which microscope 60 is focused.

In certain embodiments, controller 50 uses the z-position of base 30 from z-direction sensor 33 as an indicator of the z-position z' of an object within the eye. For example, controller 50 receives user input that ophthalmic microscope 60 is focused on an object within the eye (e.g., the retina or a floater), i.e., the object is in focus and the focal point is at the object. In response, controller 50 determines the corresponding z-position z of base 30 using z-direction sensor 33. As another example, controller 50 receives input from ophthalmic microscope 60 that is has autofocused on an object, and in response controller 50 determines the corresponding z-position z of base 30 using z-direction sensor 33.

Figure 3:
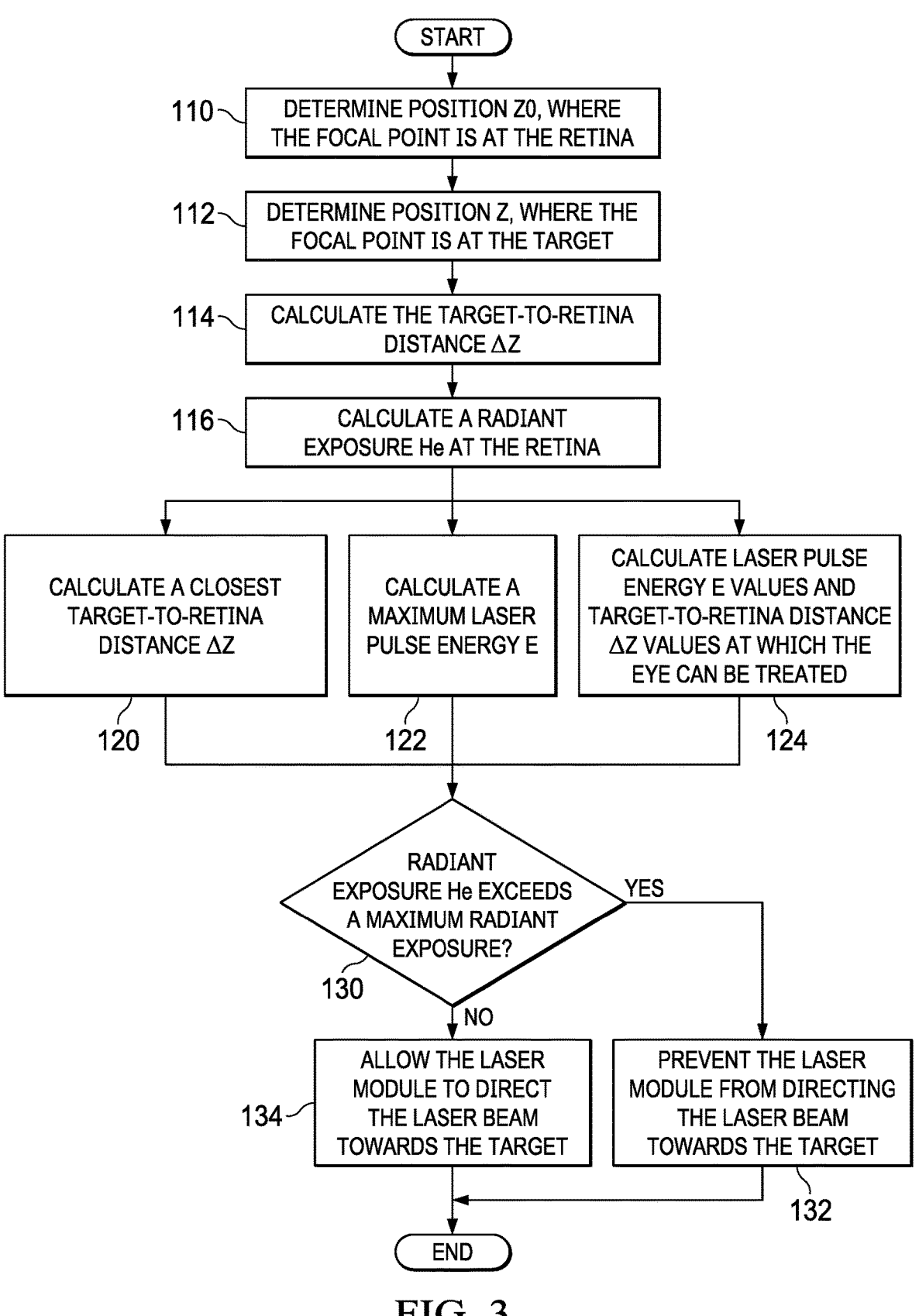
FIG. 3 illustrates an example of a method for treating an eye that may be performed by the controller of the ophthalmic laser system 10 of FIG. 1, according to certain embodiments.

FIG. 3 illustrates an example of a method for treating an eye that may be performed by controller 50 of ophthalmic laser system 10 of FIG. 1, according to certain embodiments. As an overview of the method, ophthalmic laser system 10 measures the distance of a target to the retina, determines the radiant exposure on the retina according to the distance, and provides information via a user interface and/or adjusts treatment in accordance with the radiant exposure to avoid overexposing the retina.

The method starts at step 110, where controller 50 determines z-position $Z_0$ where the focal point of the ophthalmic microscope is at the retina of the eye. In certain embodiments, controller 50 determines z-position $Z_0$ by autofocusing the focal point of the ophthalmic microscope at the retina of the eye, and determining, using the z-direction sensor, the z-position corresponding to the focal point. In other embodiments, controller 50 determines z-position Z0 by receiving user input that the focal point of the ophthalmic microscope is at the retina of the eye, and determining, using the z-direction sensor, the z-position corresponding to the focal point.

Controller 50 determines z-position Z where the focal point is at the target at step 112. In certain embodiments, controller 50 determines z-position Z by autofocusing the focal point of the ophthalmic microscope at the target within the eye, and determining, using the z-direction sensor, the z-position corresponding to the focal point. In other embodiments, controller 50 determines z-position Z by receiving user input that the focal point of the ophthalmic microscope is at the target within the eye, and determining, using the z-direction sensor, the z-position corresponding to the focal point.

The target-to-retina distance $\Delta Z$ is calculated at step 114. Controller 50 calculates the target-to-retina distance $\Delta Z$ from the difference between positions Z and $Z_0$. The radiant exposure $H_e$ at the retina is calculated at step 116. Controller 50 calculates the radiant exposure $H_e$ by determining a laser spot size of the laser beam on the retina and calculating the radiant exposure $H_e$ according to the target-to-retina distance $\Delta Z$ and the laser spot size on the retina. For example, the laser spot diameter $\Phi$ may be calculated according to $\Phi = 2 * \Delta Z * \tan \alpha$, where $\alpha$ represents the known half angle of the cone of the laser beam. The radiant exposure $H_e$ may be calculated according to:

$$H_e = 4*E/\Phi^2*\pi = 4*E/(2*\Delta Z*\tan \alpha)^2\pi \qquad (1)$$

where E is the energy of the laser pulse.

Controller 50 may optionally perform steps 120, 122, and/or 124 to calculate values at which the eye can be safely treated, given the calculated radiant exposure $H_e$. The radiant exposure $H_e$ should be less than a maximum radiant exposure, which may be determined in accordance with accepted standards. For example, the maximum radiant exposure may be set in accordance with ANSI Z80.36-2016.

Given laser pulse energy E, the closest target-to-retina distance $\Delta Z$ may be calculated at step 120 according to Equation (1). For example, given radiant exposure $H_e$ and laser pulse energy E, the minimum target-to-retina distance $\Delta Z$ such that $H_e = 4*E/(2*\Delta Z*\tan \alpha)^2\pi$ is less than the maximum radiant exposure may be determined.

Given target-to-retina distance $\Delta Z$, the maximum laser energy E may be calculated at step 122 according to Equation (1). For example, given radiant exposure $H_e$ and target-to-retina distance $\Delta Z$, the maximum laser pulse energy E such that $H_e = 4*E/(2*\Delta Z*\tan \alpha)^2\pi$ is less than the maximum radiant exposure may be determined.

More generally, laser pulse energy E values and target-to-retina distance $\Delta Z$, values at which the eye can be treated may be calculated at step 124. For example, given radiant exposure $H_e$ and a range of laser pulse energies E, a range of target-to-retina distances $\Delta Z$ such that $H_e = 4*E/(2*\Delta Z*\tan \alpha)^2\pi$ is less than the maximum radiant exposure may be determined. As another example, given radiant exposure $H_e$ and a range of suitable target-to-retina distances $\Delta Z$, a range of maximum laser pulse energies E such that $H_e = 4*E/(2*\Delta Z*\tan \alpha)^2\pi$ is less than the maximum radiant exposure may be determined.

In certain embodiments, controller 50 may output the calculated radiant exposure $H_e$ and/or calculated values from steps 120, 122, and/or 124 to the operator via a user interface. In the embodiments, controller 50 may also receive user input from the operator selecting a calculated value and adjusting system 10 according to the selected value.

Controller 50 may determine that the radiant exposure $H_e$ exceeds a maximum radiant exposure at step 130. If the radiant exposure $H_e$ exceeds the maximum radiant exposure, controller 50 moves to step 132 to prevent the laser device from directing the laser beam towards the target. Additionally or alternatively, controller 50 may provide a warning (e.g., audio and/or visual) via a user interface. If the radiant exposure $H_e$ does not exceed the maximum radiant exposure, controller 50 moves to step 134 to allow the laser device to direct the laser beam towards the target. The method then ends.

A component (such as controller 50) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser system, comprising:
a laser device configured to direct a laser beam towards a target within an eye, the eye having a retina, an axis of the eye defining a z-axis, a z-position being a position relative to the z-axis;
an ophthalmic microscope configured to receive light from a focal point within the eye to provide an image of an object at the focal point;
a z-direction sensor configured to determine the z-position corresponding to the focal point of the ophthalmic microscope; and
a controller configured to:
determine a position $Z_0$, the z-position where the focal point of the ophthalmic microscope is at the retina of the eye;
determine a position Z, the z-position where the focal point of the ophthalmic microscope is at the target within the eye;
calculate a target-to-retina distance $\Delta Z$ according to a difference between the position Z and the position $Z_0$;
calculate a radiant exposure $H_e$ at the retina according to the target-to-retina distance $\Delta Z$;
determine whether the radiant exposure $H_e$ exceeds a maximum radiant exposure;
if the radiant exposure $H_e$ exceeds the maximum radiant exposure, prevent the laser device from directing the laser beam towards the target within the eye; and
otherwise, allow the laser device to direct the laser beam towards the target within the eye.

2. The ophthalmic laser system of claim 1, the z-direction sensor configured to determine the z-position corresponding to the focal point of the ophthalmic microscope by:
detecting the z-position of a base of the ophthalmic microscope.

3. The ophthalmic laser system of claim 1, the controller configured to determine the position $Z_0$, the z-position where the focal point of the ophthalmic microscope is at the retina of the eye, by:
autofocusing the focal point of the ophthalmic microscope at the retina of the eye; and
determining, from the z-direction sensor, the z-position corresponding to the focal point.

4. The ophthalmic laser system of claim 1, the controller configured to determine the position $Z_0$, the z-position where the focal point of the ophthalmic microscope is at the retina of the eye, by:
receiving user input that the focal point of the ophthalmic microscope is at the retina of the eye; and
determining, from the z-direction sensor, the z-position corresponding to the focal point.

5. The ophthalmic laser system of claim 1, the controller configured to determine the position Z, the z-position where the focal point of the ophthalmic microscope is at the target within the eye, by:
autofocusing the focal point of the ophthalmic microscope at the target within the eye; and
determining, from the z-direction sensor, the z-position corresponding to the focal point.

6. The ophthalmic laser system of claim 1, the controller configured to determine the position Z, the z-position where the focal point of the ophthalmic microscope is at the target within the eye, by:
receiving user input that the focal point of the ophthalmic microscope is at the target within the eye; and
determining, from the z-direction sensor, the z-position corresponding to the focal point.

7. The ophthalmic laser system of claim 1, the controller configured to calculate the radiant exposure $H_e$ according to the target-to-retina distance $\Delta Z$ by:
determining a laser spot size of the laser beam on the retina; and
calculating the radiant exposure $H_e$ according to the target-to-retina distance $\Delta Z$ and the laser spot size of the laser beam.

8. The ophthalmic laser system of claim 1, the controller further configured to:
calculate a closest target-to-retina distance $\Delta Z$ at which the eye can be treated, given a laser pulse energy E of the laser beam.

9. The ophthalmic laser system of claim 1, the controller further configured to:
calculate a maximum laser pulse energy E at which the eye can be treated, given the target-to-retina distance $\Delta Z$.

10. The ophthalmic laser system of claim 1, the controller further configured to:
calculate a range of laser pulse energy E values and a range of target-to-retina distance $\Delta Z$ values at which the eye can be treated.

11. An ophthalmic laser system, comprising:
a laser device configured to direct a laser beam towards a target within an eye, the eye having a retina, an axis of the eye defining a z-axis, a z-position being a position relative to the z-axis;
an ophthalmic microscope configured to receive light from a focal point within the eye to provide an image of an object at the focal point;
a z-direction sensor configured to determine the z-position corresponding to the focal point of the ophthalmic microscope by detecting the z-position of a base of the ophthalmic microscope; and
a controller configured to:
determine a position $Z_0$, the z-position where the focal point of the ophthalmic microscope is at the retina of the eye by:
autofocusing the focal point of the ophthalmic microscope at the retina of the eye or receiving user input that the focal point of the ophthalmic microscope is at the retina of the eye; and
determining, from the z-direction sensor, the z-position corresponding to the focal point;
determine a position Z, the z-position where the focal point of the ophthalmic microscope is at the target within the eye, by:
autofocusing the focal point of the ophthalmic microscope at the target within the eye or receiving user input that the focal point of the ophthal-
mic microscope is at the target within the eye; and
determining, from the z-direction sensor, the z-po-
sition corresponding to the focal point;
calculate a target-to-retina distance $\Delta Z$ according to a
difference between the position Z and the position
$Z_0$;
calculate a radiant exposure $H_e$ at the retina according
to the target-to-retina distance $\Delta Z$ by:
determining a laser spot size of the laser beam on the
retina; and
calculating the radiant exposure $H_e$ according to the
target-to-retina distance $\Delta Z$ and the laser spot size
of the laser beam:
calculate a closest target-to-retina distance $\Delta Z$ at which
the eye can be treated, given a laser pulse energy E
of the laser beam;
calculate a maximum laser pulse energy E at which the
eye can be treated, given the target-to-retina distance
$\Delta Z$;
calculate a range of laser pulse energy E values and a
range of target-to-retina distance $\Delta Z$ values at which
the eye can be treated;
determine whether the radiant exposure $H_e$ exceeds a
maximum radiant exposure;
if the radiant exposure $H_e$ exceeds a maximum radiant
exposure, prevent the laser device from directing the
laser beam towards the target within the eye; and
otherwise, allow the laser device to direct the laser beam
towards the target within the eye.

\* \* \* \* \*